United States Patent [19]

Marcus et al.

[11] Patent Number: 5,295,484
[45] Date of Patent: Mar. 22, 1994

[54] APPARATUS AND METHOD FOR INTRA-CARDIAC ABLATION OF ARRHYTHMIAS

[75] Inventors: Frank I. Marcus; Kullervo H. Hynynen, both of Tuscon, Ariz.

[73] Assignee: Arizona Board of Regents for and on Behalf of the University of Arizona, Tucson, Ariz.

[21] Appl. No.: 885,190

[22] Filed: May 19, 1992

[51] Int. Cl.$^5$ .............................................. A61B 8/00
[52] U.S. Cl. .............................. 128/660.03; 128/696; 128/702; 128/710; 606/27; 601/2; 607/115
[58] Field of Search ............. 128/24 AA, 660.03, 696, 128/702, 399, 804, 710, 783, 784, 786; 606/27, 28, 128; 604/22

[56] References Cited

U.S. PATENT DOCUMENTS

| 4,526,168 | 7/1985 | Hassler et al. | 128/660.03 |
|---|---|---|---|
| 4,641,649 | 2/1987 | Walinsky et al. | 128/303.1 |
| 4,924,863 | 5/1990 | Sterzer | 606/27 |
| 4,938,217 | 7/1990 | Lele | 128/399 |
| 4,940,064 | 7/1990 | Desai | 128/784 |
| 5,029,588 | 7/1991 | Yock et al. | 128/660.03 |

OTHER PUBLICATIONS

Siegel, R. J., Ultrasonic Plaque Ablation, vol. 78, No. 6, pp. 1443-1448.
Siegel, R. J., In Vivo Ultrasound Arterial Recanalization of Atherosclerotic Total Occlusions.
Siegel, R. J., The Lancet, pp. 772-774, Sep. 30, 1989.
Rosenschein, U., Journal of the American College of Cardiology, vol. 15, No. 3, pp. 711-717, 1990.
Rosenschein, U., Circulation, vol. 83, No. 6, pp. 1976-1986, 1991.
M. Marberger, Urologic Clinics of North America, vol. 10, No. 4, pp. 729-741, 1983.
Hodgson, W. J. B., American Journal of Gastroenterology, vol. 72, No. 2, pp. 133-140, 1979.
Mowry, R., Otolaryngol Head Neck Surg, vol. 90, pp. 305-309, 1982.
Brown, A. H., British Medical Jouranl, vol. 3, pp. 274-277, 1972.
Potkin, B. N., Circulation, vol. 81, No. 5, pp. 1575-1585, 1990.
Tobis, J. M., Circulation, vol. 83, No. 3, pp. 913-926, 1991.
Sheikh, K. H., American Journal of Cardiology, vol. 67, pp. 817-822, 1991.
Yock, P. G., Journal of the American college of Cardiology, vol. 17, No. 6, pp. 39B-45B, 1991.
Diederich, C. J., IEEE Transactions on Biomedical Engineering, vol. 36, No. 4, pp. 432-438, 1989.

*Primary Examiner*—Ruth S. Smith
*Attorney, Agent, or Firm*—Rosenbaum & Associates

[57] ABSTRACT

The present invention employs ultrasonic energy delivered to myocardial tissue at frequencies sufficient to destroy the myocardial tissue implicated in the arrhythmic. More specifically, the present invention comprises an ultrasonic transducer mounted on a distal end of a catheter and at least one electrode associated with the distal end region of the catheter. The ultrasonic transducer may be a single crystal transducer or a phased array crystal transducer.

31 Claims, 2 Drawing Sheets

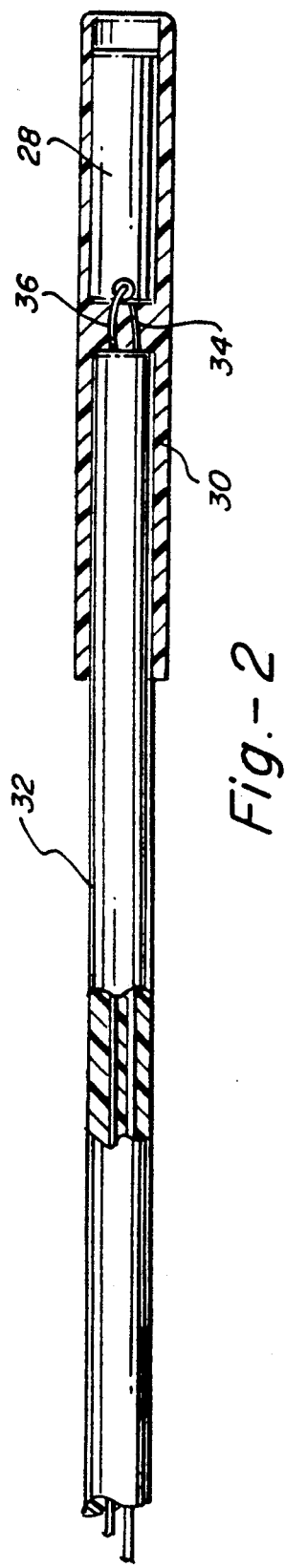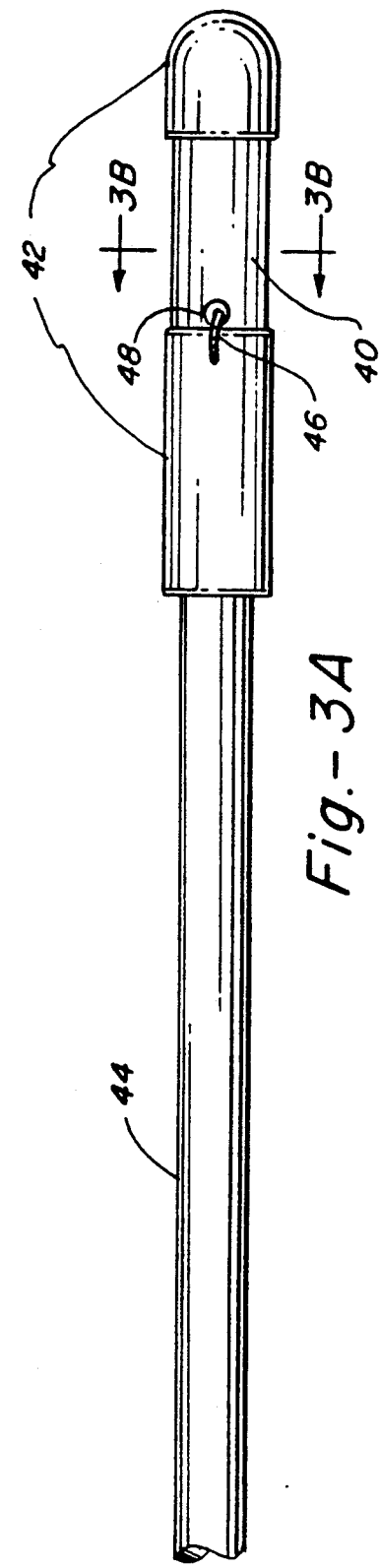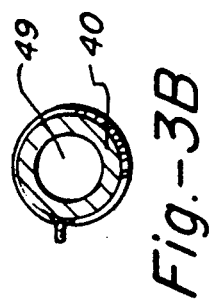

APPARATUS AND METHOD FOR INTRA-CARDIAC ABLATION OF ARRHYTHMIAS

BACKGROUND OF THE INVENTION

The present invention relates generally to an apparatus and method for elimination of abnormal heart rhythms or arrhythmias. More particularly, the present invention relates to an ultrasonic catheter and method for delivering ultrasonic energy to the heart for selectively ablating cardiac tissue to restore normal heart rhythms.

Currently there are a number of medical and surgical treatments for cardiac arrhythmias. Medical treatments are principally through the use of antiarrhythmic drugs which slow intra-cardiac impulses conduction or refractoriness which sustains an arrhythmia once started. All antiarrhythmic drugs have undesirable side effects. For example, nausea, vomiting or diarrhea occur in about 40-60% of patients treated with quinidine. Lupus, an immunoreactive syndrome characterized by high antinuclear titers in the blood, diffuse arthralgia, pleural and pericardial effusion occur in about 30% of the patients taking procainamide for longer than six months. Only recently have the proarrhythmic effects of these drugs begun to be fully appreciated. For example, in a recent National Institutes of Health sponsored study it was found that post-myocardial infarction patients who were treated with two of three antiarrhythmic drugs had a threefold higher sudden death mortality than those given placebo.

Surgical treatments offer a second therapeutic option in the treatment of cardiac arrhythmias. Surgical methods permit localization of the origin of the arrhythmia or a critical part of the electrical conduction circuit during open heart surgery. When accessed in this manner, the arrhythmia may be eliminated by excising myocardial tissue or ablating the tissue using cryothermia or laser. For example, some patients are born with an anomalous connection between the atrium and ventricle known as Wolff Parkinson White Syndrome. These anomalous conduction pathways can be surgically cut during open heart surgery.

Surgical treatment of arrhythmias has an associated mortality of less than 1% in treating patients with Wolff Parkinson White Syndrome and morbidity is not significant. However, surgical treatment of patients with ventricular arrhythmias has an associated 10% operative mortality. Open heart surgery for the treatment of cardiac arrhythmias is clearly not a desirable therapeutic modality.

Devices, commonly known as "pacemakers", are medical devices which have become widely used in the treatment of ventricular cardiac arrhythmias. These devices consist of programmable implanted units that either stimulate cardiac contractions by a train of electrical impulses or depolarize the heart to stop the arrhythmia, at which time normal sinus rhythm resumes. The devices which depolarize the heart are known as automatic, implantable cardioverter defibrillators (AICD) and have become accepted for treatment of ventricular arrhythmias which do not respond to drug treatment. Implanting AICD devices requires open chest surgery with the total cost of the device and implantation ranging from $35-50,000. Infection which requires removal of the device occurs in 2-4% of the cases and operative mortality ranges from 1-4%.

Myocardial tissue ablation is another therapeutic modality for treatment of arrhythmias. Tissue ablation techniques generally use an energy source to transmit either electrical or thermal energy to selected myocardial tissue to cause an ablative effect.

Current tissue ablation techniques include use of one of i) direct current; ii) radio frequency energy; iii) microwave energy; iv) cryothermia; or v) laser energy. In 1982 two separate investigators introduced the use of catheters to deliver a direct current electrical charge to myocardial tissue. Endocardial catheters were inserted percutaneously to the atrial-ventricular (AV) node region. The procedure attempted to totally eliminate electrical conduction between the atrium and the ventricle and is performed to treat atrial fibrillation or other arrhythmias involving rapid conduction of electrical impulses around or through the AV node. Subsequently, catheter-based delivery of direct current energy was extended to treat anomalous pathways as well as ventricular arrhythmias.

The use of direct current energy entails the endocardial generation of several hundred joules through application of about 2,000-4,000 volts of electricity for a few milliseconds. Tissue damage due to direct current shock may occur due to thermal injury, barotrauma or the induction of an electrical field in the tissue. A principal disadvantage associated with use of direct current energy is the difficulty of controlling the application of energy. The direct current myocardial tissue ablation techniques must be performed under general anesthesia due to the painful muscular contractions associated with application of the direct current energy. Complications include the danger of inducing ventricular tachycardia in 5% of the patients or perforation of the heart, tamponade, hypotension, shock and cardiac embolization, which are noted in about 15% of the patients. Use of direct current energy has also been known to damage the catheters used to deliver the voltages. Catheters used for application of direct current energy for myocardial tissue ablation are usually diagnostic electrophysiological catheters which are not made to withstand the applied voltages. As a consequence, the damaged catheter may generate an electrical discharge at a non-intended location.

In 1986 the use of radio frequency energy for cardiac ablation was introduced. This method has met with widespread acceptance and success in treating supraventricular arrhythmias. As result, radio frequency energy has become the dominant energy source used for myocardial tissue ablation. Catheter-based delivery of radio frequency energy causes thermal tissue damage as a result of the electrical current flow to the tissue. Radio frequency energy uses sinusoidal electrical current, in the range of 40-60 volts, directly applied to the tissue. Limitations on the use of radio frequency include low energy generation which limits the size of the ablated area, the resulting need for precise intracardiac localization, the formation of blood clots on the electrode once the electrode reaches 90°-100° C. and the decrease of power delivered to the tissue as the energy source moves away from the tissue. The latter factor is, perhaps, the most limiting. Since power delivered to the tissue decreases to the fourth power from the point of delivery from the catheter, the depth of tissue penetration is limited. This renders the radio frequency techniques unsuitable for certain arrhythmias, especially, those originating in the left ventricle. Additionally, there has been no mapping technique developed for use with the radio frequency catheters which permit rapid and precise localization of the energy source relative to the myocardium.

Microwave energy is under investigation as an energy source for cardiac tissue ablation. However, many of the practical limitations associated with radio frequency energy apply to microwave energy. As with radio frequency energy, power delivered by microwave energy decreases exponentially from the point of delivery, therefore tissue penetration may be limited, albeit to a lesser degree than with radio frequency energy. Additionally, because of its relatively long wavelength at the frequencies under investigation, microwave energy is extremely difficult to focus.

Cryoprobes, cooled to $-70°$ C., are commonly used to ablate cardiac tissue during open heart surgery. However, to deliver this degree of cooling to the tip of the catheter, the catheter has to be so large in diameter (11–12 French), that perforation of the cardiac tissue is a danger.

Finally, laser energy delivered through a pervenous catheter has been used to successfully ablate the AV node in canine experiments. Despite this success, there remains a serious concern relating to heart perforation, optical fiber tip deterioration, fragility of the optical fiber, and the lack of optimal portable instrumentation for laser energy generation, monitoring and cardiac mapping.

While the use of catheter-based energy delivery systems in ablation of myocardial tissue are clearly known, each of the systems known, used or under investigation suffer from one or more of the above mentioned shortcomings. The present invention has been developed to provide an alternative method and apparatus for intra-cardiac ablation of myocardial tissue to eliminate cardiac arrhythmias.

SUMMARY OF THE INVENTION

The present invention employs ultrasonic energy delivered to myocardial tissue at frequencies sufficient to destroy the myocardial tissue implicated in the arrhythmia. More specifically, the present invention comprises an ultrasonic transducer mounted on a distal end of a catheter and at least one electrode associated with the distal end region of the catheter. The ultrasonic transducer may be a single crystal transducer or a phased array crystal transducer. Ultrasonic transducers adapted for use in the invention are those capable of generating frequencies in the 1–40 MHz range under an applied electrical energy of 2 watts or above. Then at least one electrode associated with the catheter is used to map the position and orientation of the ultrasound transducer in the heart based upon electrical conduction in the heart tissue. Electrodes suitable for use are those of the type capable of receiving electrical signal outputs from the myocardial tissue and transmitting the signals to a display or recorder for real-time visualization by a medical practitioner.

The method of the invention generally entails the steps of i) introducing the catheter into the heart through a venous or arterial route; ii) electrically mapping the position and orienting the catheter and transducer in the heart; iii) determining the myocardial tissue area to be treated; iv) ultrasonically coupling the transducer to the selected myocardial tissue area; and v) applying electrical energy to the ultrasound transducer to ablate the selected tissue area in order to eliminate the arrhythmia focus or a portion of the intracardiac electrical circuit that is necessary to sustain the arrhythmia, as indicated by elimination of the arrhythmia or inability to electrically stimulate the abnormal heart rhythm.

These and other objects, features and advantages of the present invention will become more apparent to those skilled in the art from the following more detailed description of the present invention taken with reference to the accompanying drawings.

BRIEF DESCRIPTION OF THE DRAWINGS

FIG. 2 is a side elevational view of a first embodiment of an ultrasound catheter in accordance with the present invention.

FIG. 3A is a side elevational view of a second embodiment of an ultrasound catheter in accordance with the present invention.

FIG. 3B is a cross-sectional diagrammatic view taken along line 3B-3B of FIG. 3A.

DETAILED DESCRIPTION OF THE PREFERRED EMBODIMENTS

Figure 1:
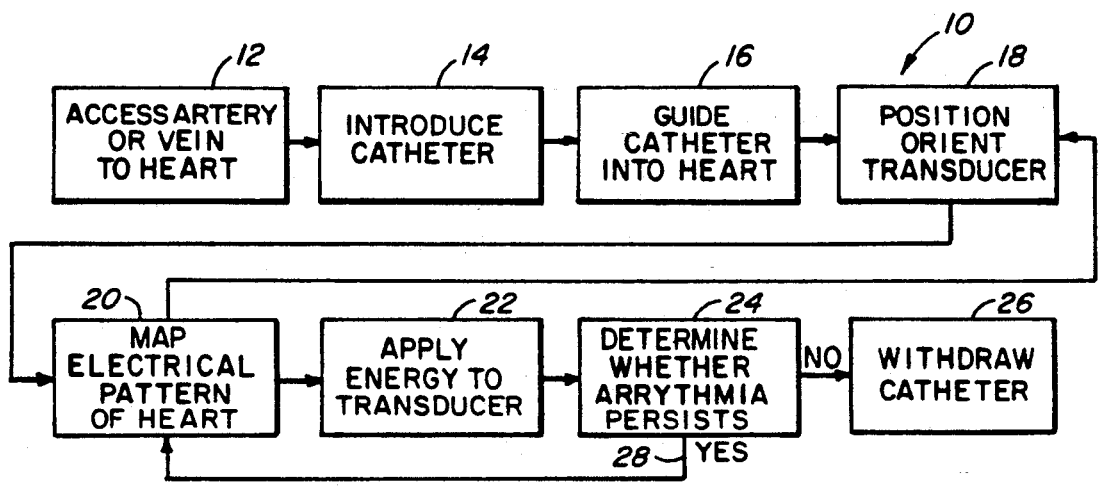
FIG. 1 is a process flow diagram diagrammatically illustrating the method of intra-cardiac ablation of arrhythmias.

The inventive method 10 for intra-cardiac ablation of arrhythmias is illustrated in FIG. 1. In accordance with this method, either a vein or an artery which leads to the heart and affords ease of access to either the pulmonary vein or the aorta is surgically accessed 12. A catheter, of the type described below having an ultrasound transducer and at least one electrode associated with a distal end area of the catheter, is introduced 14 percutaneously into the accessed vein or artery. The catheter is guided through the accessed blood vessel and into an intra-cardiac region of the heart 16. In accordance with the best mode known to the inventors, the catheter is fluoroscopically guided through the accessed vessel into the heart. Once in the heart, the catheter is positioned and the transducer oriented 18 toward the myocardial tissue to be treated. An electrical mapping 20 of conduction pattern in the heart is made using the at least one electrode on the catheter. The at least one electrode on the catheter can also be used to induce an abnormal heart rhythm in order to perform the electrical mapping of a nonpersistent arrhythmia. The electrical mapping 20 aids in positioning and orienting the transducer 18 relative to the myocardial tissue to be treated. The transducer may also be oriented by attaching a thermocouple to the active side of the ultrasound transducer to determine if the transducer is in contact with the tissue wall. Once positioned with the transducer oriented toward the selected myocardial tissue, the electrical energy is applied to the ultrasound transducer 22 to cause the transducer to resonate and emit ultrasound energy directed toward the selected myocardial tissue. After application of the ultrasound energy at a preselected frequency, power and duration, signals received by the at least one electrode will provide feedback to enable the medical practitioner to determine whether the arrhythmia persists 24. In addition, electrical stimulation to this or other electrodes in the heart to try to induce the abnormal heart rhythm in non-persistent arrhythmias will further indicate the success or lack thereof of the ultrasound created lesion in that location. If the arrhythmia induced or otherwise, no longer persists, the catheter is withdrawn 26. Conversely if the arrhythmia persists 27, the electrode mapping step 20 is repeated to confirm position and orientation of the ultrasound transducer relative to the myocardium, and the application of ultrasonic energy 22 repeated until normal sinus rhythm is restored or the arrhythmia cannot be restarted by repeat cardiac electrical stimulation 26.

A first preferred embodiment of the ultrasound catheter in accordance with the present invention is illustrated in FIG. 2. An ultrasound transducer 28 is embedded in a plastic mount 30. The plastic mount 30 also joins a flexible catheter 32 to the ultrasound transducer 28 and carries wires 34, 36, which run the length of the catheter 32. A first wire 34, is electrically coupled, such as by soldering, to the back surface or packing surface of the ultrasound transducer 28. A second wire 36, is electrically coupled, such as by soldering, to the front surface or active surface of ultrasound transducer 28. At least one electrode (not shown) is mounted on the catheter 32, in close proximity to the ultrasound transducer 28. The at least one electrode receives electrical cardiac signals to enable the positioning of the ultrasound transducer 28 for ablation of cardiac tissue. Wires (not shown) traverse the length of the catheter 32 and electrically connect the electrode with external cardiac monitoring equipment, such as an electrocardiograph. The front or active surface of ultrasound transducer 28 preferably forms part of the external surface of plastic mount 30, but may have a relatively thin covering disposed over the ultrasound transducer 28 for protective purposes.

The back surface or packing side (not shown) of ultrasound transducer 28 is attached to plastic mount 30 with a low or high impedance backing adjacent the packing surface or back surface of the transducer. This may be facilitated by an air pocket or space located between the ultrasound transducer 28 and plastic mount 30. It is important that there be a high degree of impedance contrast between active and packing surfaces of the ultrasound transducer 28. The energy generated by the ultrasound transducer 28 must have sufficient power to ablate cardiac tissue. Accordingly, it is necessary that a maximal amount of energy, generated by the transducer 28, be directed from the active surface of the transducer 28. To maximize power output, such as that generated by a narrow band frequency output, there must be an impedance contrast between the active and packing surfaces of the ultrasound transducer.

Wires 34, 36 are used to apply electrical energy to the ultrasound transducer 28 to cause it to resonate and emit ultrasound energy to the cardiac tissue. When electrical energy is applied to ultrasound transducer 28, the low or high impedance backing directs substantially all of the narrow band frequency ultrasound energy to the active front surface of ultrasound transducer 28. The directed ultrasound energy ablates the targeted cardiac tissue and thereby eliminates the arrhythmia.

Those skilled in the art will understand that, in accordance with the first preferred embodiment, illustrated in FIG. 2, the flat or planar ultrasound transducer 28 will generate collimated ultrasound energy which will be concentrated in an area substantially corresponding to that of the ultrasound transducer 28 surface area.

A second preferred embodiment of the ultrasound cardiac ablation transducer is shown in FIGS. 3A and 3B. FIG. 3A shows a side elevational view of a hollow cylindrical ultrasound transducer 40 mounted in a plastic mount 42. Catheter 44, which contains two wires which run the length of the catheter 44 is also mounted to plastic mount 42. Both wires exit the catheter on the end of the catheter nearest to the ultrasound transducer and are connected to the ultrasound transducer. Wire 46 exits the catheter 44 through plastic mount 42 and is connected to ultrasound transducer 40 at solder joint 48. A second wire (not shown) is connected to the back or packing side of ultrasound transducer 40, in this case the annular inside surface of the hollow cylinder which constitutes the ultrasound transducer 40. FIG. 3B shows a cross-section of the ultrasound transducer crystal 40 in FIG. 3A. The annular lumen 49 of the ultrasound transducer 40 contains air which functions as an impedance backing, thereby facilitating the generation of a narrow band frequency needed to direct substantially all of the ultrasound energy to the tissue to be ablated. In addition, like the first embodiment discussed above, at least one electrode (not shown) is associated with the catheter 44, in close proximity to the ultrasound transducer 40, to permit mapping of the electrical signals of the heart. Cardiac mapping provides a means for positioning the ultrasound transducer 40 near the cardiac arrhythmia to be ablated. Moreover, the at least one electrode can also be electrically stimulated to induce a nonpersistent abnormal heart rhythm thereby functioning as an indicator of whether or not the tissue ablation was successful in eliminating the arrhythmia. The energy is emitted radially from the transducer 40 and is non-concentrating and non-collimated.

Figure 4:
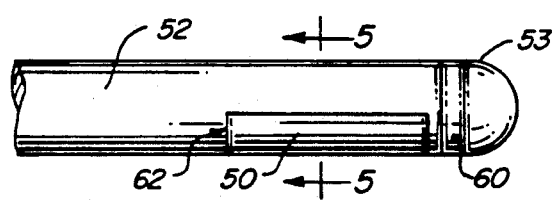
FIG. 4 is a side elevational view of a third embodiment of an ultrasound catheter in accordance with the present invention.
Figure 5:
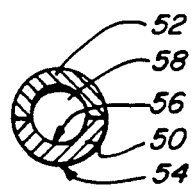
FIG. 5 is a cross-sectional diagrammatic view taken along line 5—5 of FIG. 4.

A third preferred embodiment of an ultrasound transducer catheter in accordance with the present invention is illustrated in FIGS. 4 and 5. This embodiment of transducer 50 comprises a phased array of annular half cylinder transducer elements which are embedded in or mounted on or in association with catheter 52. At least one electrode 53 is mounted on the surface of catheter 52 in order to perform the mapping of the electrical pattern of the heart as previously discussed with FIG. 1. The active surface 54 of transducer 50 forms an external part of catheter 52. The backside, or packing side 56, of transducer 50 is mounted to catheter 52 such that a low impedance backing, such as air or gas, or high impedance backing, such as metal, is formed behind transducer 50. The backing encompasses the area exemplified by opening 58 between catheter 52 and packing side 56 of transducer 50. The impedance backing 58 is different and distinct from the impedance of the catheter surface which comes into contact with the front surface 60 and rear surface 62 of transducer 50 thereby generating a narrow band frequency when energy is applied to the transducer 50. The energy is emitted radially from the transducer array and by introducing a proper phase shift between the radio frequency voltages which are driving each of the transducer elements, the energy can be focussed along the length of the applicator at a desired radial distance.

Figure 6:
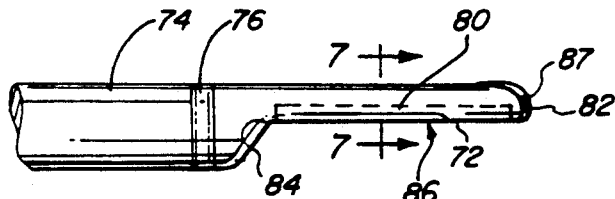
FIG. 6 is a cross-sectional diagrammatic view of a fourth embodiment of an ultrasound catheter in accordance with the present invention.
Figure 7:
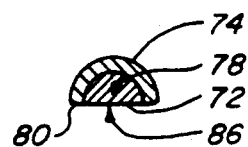
FIG. 7 is a cross-sectional diagrammatic view taken along line 7—7 of FIG. 6.

FIGS. 6 and 7 represent a fourth preferred embodiment of the ultrasound transducer catheter in accordance with the present inventive method and apparatus. Transducer 72 comprises a phased array of transducer elements mounted on or in association with catheter 74. At least one electrode 76 is also mounted on catheter 74 to enable mapping of the electrical pattern of the heart or the electrical inducement of a nonpersistent abnormal heart rhythm in order to locate the arrhythmia and determine if it still exists after ablation. If tissue ablation with the ultrasound transducer 72 is successful, electrical stimulation of the at least one electrode 76 will result in the inability to induce the abnormal arrhythmia. The backside or packing surface 78 of ultrasound transducer 72 is mounted to catheter 74 so that a low or high impedance backing 80 is created between the ultrasound transducer 72 and the catheter 74. Epoxy or a similar functioning compound is used to mount the front and rear surfaces 82, 84 of the ultrasound transducer 72 to the catheter 74. When energy is applied to the ultrasound transducer 72, it generates a narrow band energy which directs substantially all of the energy to the active surface 86 of the ultrasound transducer 72. By introducing a proper phase shift between the radio frequency voltages which are driving each of the transducer elements, the energy can be focussed at a desired depth and location in front of the transducer. Because of the planar orientation of the transducer 72, the ultrasonic energy is highly collimated and directed to a surface area roughly corresponding to that of the transducer 72. An additional ultrasound transducer may be mounted on the catheter to assist in mapping the electrical patterns of the heart and/or ablate cardiac tissue. A small ultrasound transducer 87 like that just described is located at the tip of catheter 74. Ultrasound transducer tip 87 is also capable of inducing a nonpersistent abnormal arrhythmia.

Figure 8:
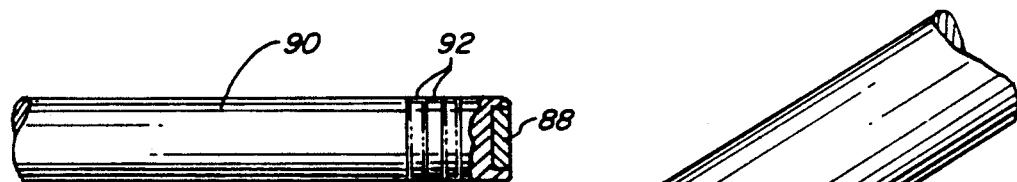
FIG. 8 is a side elevational view of a fifth embodiment of ultrasound catheter in accordance with the present invention.
Figure 9:
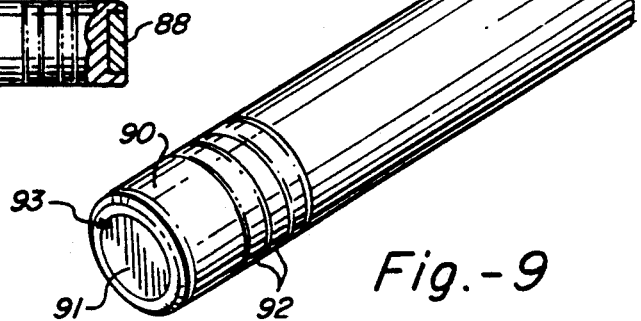
FIG. 9 is a perspective fragmentary view of the fifth embodiment of the ultrasound catheter in accordance with the present invention.

A fifth preferred embodiment of the inventive transducer catheter is illustrated in FIGS. 8 and 9. Ultrasound transducer 88 is represented by an axially oriented ultrasound transducer 88 which is mounted on or associated with catheter 90. In addition, at least one electrode 92 is mounted on the catheter. The at least one electrode 92 may be capable of both mapping the electrical patterns of the heart and inducing an abnormal heart rhythm upon electrical stimulation. FIG. 9 is a perspective view of the tip of the catheter 90. The top surface 91 of the ultrasound transducer 88 forms an external part of the catheter tip while the back or packing surface of the ultrasound transducer 88 is contained inside the catheter 90. A low or high impedance backing is provided on the packing side of the ultrasound transducer 88. Lateral side edge 93 of ultrasound transducer 88 is mounted in or to an annular opening in the catheter 90 with epoxy or a similar functioning compound. As previously discussed, an impedance difference between the active surface and packing surface of the transducer 88 facilitates generation of a narrow band frequency which directs maximal energy to the active surface 1 of the transducer 88.

Although the embodiments of the present invention discussed so far all comprise ultrasound transducers which form some part of the surface of the catheter, alternative embodiments of those embodiments discussed would further comprise a thin layer of nonconductive material over those surfaces of the transducer which are exposed as part of the outside surface of the catheter. However, the low or high impedance backing adjacent the packing side of the transducer and the impedance differential between the active side and packing sides of the catheter remain a significant aspect of each embodiment. In addition, although the previously described embodiments each comprise electrodes for mapping the electrical signals of the heart, any other means for mapping such signals that are known in the art may also be used including transducer elements. A separate ultrasound transducer may be used for mapping or imaging in addition to the ablating ultrasound transducer. For example, in the embodiment illustrated in FIGS. 6 and 7, in which a phased array ultrasound transducer is provided, certain of the transducer elements in the phased array may be partitioned with a non-conductive material and thereby independently controlled to generate imaging frequencies, and provide either ultrasound mode A or mode B signal feedback. Alternatively, the same ultrasound transducer may be used with different frequencies or assembled in a phased array in order to perform both cardiac signal imaging and cardiac tissue ablation.

A Phase I study was conducted from January 1992 to March 1992 to determine the feasibility of prototype ultrasound transducer catheters for cardiac tissue ablation. Two groups of ultrasound transducer catheters were employed in four animal studies using the mongrel dog model. The objective was to produce cardiac muscle lesions of sizes at least 0.5 centimeters squared. All animals were properly anesthetized. The following protocol was used in all four animal studies: 1) open the dog chest through sternotomy, 2) cut open the pericardium, 3) suture the pericardium to the chest wall to make a "sack" and fill it with degassed saline, 4) place the transducer on the surface of the epicardium and deliver the ultrasound energy on the epicardium, and 5) make a purse string around the right and left appendage of the heart and advance the transducer into the right and left ventricles of the heart and deliver the ultrasound energy on the endocardium.

Results for the four previously described non-limiting animal studies were favorable. In study 1, two rectangular transducers made of PZT crystal material (Edo company UT) with frequencies of 5.6 MHz and 9.15 MHz, respectively, were used to deliver ultrasound energy. Six energy deliveries were made, two on the epicardium and four on the endocardium. The deliveries were from 30 to 60 seconds in duration and ranged from 5 Watts to 30 Watts. Three visible lesions were created. One was on the left ventricle and measured 1.7 cm. at the epicardial base and 0.8 cm. in depth, another was on the left ventricle close to the apex and measured 2.0 cm. at the epicardial surface and 0.6 cm. in depth, and the third was made on the papillary muscle of the right ventricle.

In study 2, two transducers were used with similar frequencies and shapes as those in study 1, but made of EBL#1 crystal material (Edo company UT) instead of PZT crystal material. Eight energy deliveries were made, but following the deliveries, the heart was preserved in formalin for 4 days before cutting it open to examine it for lesions. The duration of the deliveries were from 30 to 60 seconds with power ranging from 27 to 30 Watts. One rectangular shaped lesion in the right ventricle lateral wall epicardium measured 1.5 cm. at the epicardial surface and 0.8 cm. in depth while another rectangular shaped lesion in the left ventricle close to the apex measured 1.8 cm. at the epicardium and 0.2 cm. in depth. Other lesions formed a sharp triangular area of 1.5 cm. with a 1.1 cm. depth and a sharp oval area measuring 1.5 cm with a 0.3 cm. depth.

A third study used three rectangular shaped transducers made of EBL#1 crystal material (Edo company UT) with frequencies of 14.4 MHz, 9.15 MHz and 5.63 MHz respectively. Two thermocouples were mounted to the back and surface of the 9.15 MHz transducer to monitor the temperature during the delivery of ultrasound energy. Seven energy deliveries were made for periods of 60 seconds each ranging in power from 9 to 37 Watts. Three visible lesions were created. Delivering 13 Watts of electrical power to the 14.4 MHz transducer produced a lesion in the right ventricle measuring 13×8×4 mm. Electrical power of 37.5 Watts and reflected power of 27 Watts produced a first lesion on the epicardium measuring 10×6 mm. The temperature reading from the thermocouple was 70.9 degrees C. Electrical power of 31 Watts and reflected power of 17.5 Watts produced a second "V"-shaped lesion on the epicardium measuring 8×26×3 mm with temperature measuring over 200 degrees C.

The fourth and final study in the protocol employed two rectangular shaped transducers made with EBL#1 crystals (Edo company UT) with frequencies of 5.73 MHz and 9.11 MHz respectively. Three ultrasound energy deliveries were executed on the endocardium of the left ventricle. Two visible lesions were formed. Both lesions resulted from applying 26 Watts of electrical power to the 9.11 MHz transducer. Ultrasound energy delivery for a period of 35 seconds created a rectangularly shaped lesion which measured 30×9×6 mm. while a 60 second energy delivery created a rectangularly shaped lesion measuring 18×11×3 mm.

The prototype transducers used in the studies were very rigid. Those energy deliveries which did not produce visible lesions were affected by the difficulty in placing a rigid transducer on a constantly moving heart. The failure to produce certain lesions resulted from improper placement of the transducer. The previously described non-limiting examples utilizing the apparatus and method for intra-cardiac ablation of arrhythmias are provided to show the feasibility and functioning of the present invention.

While preferred embodiments of the invention have been shown and described, it will be apparent to those skilled in this art that various modifications may be made in these embodiments without departing from the spirit of the present invention.

What is claimed is:

1. A method for intra-cardiac ablation of arrhythmias in a subject in need thereof, comprising the steps of:
   A. Guiding a catheter, having an ultrasonic transducer mounted on a distal end thereof and means for sensing electrical cardiac signals, into a heart of the subject;
   B. sensing electrical cardiac signals in the subject with said sensing means;
   C. positioning the catheter to place the ultrasonic transducer in close proximity to a cardiac tissue region to be treated in response to sensed cardiac signals;
   D. activating the ultrasonic transducer to direct ultrasonic energy at the cardiac tissue region to be treated, thereby generating thermal energy in the cardiac tissue; and
   E. heating the cardiac tissue to a temperature and depth sufficient to ablate the cardiac tissue, thereby ablating the arrhythmia.

2. The method of claim 1, wherein said step of sensing electrical cardiac signals further comprises the step of stimulating and sensing electrical cardiac signals in the subject.

3. The method of claim 2, wherein said step of sensing electrical cardiac signals further comprises the step of providing at least one electrode associated with said catheter, said at least one electrode being electrically coupled to recording means for recording electrical impulses of the heart.

4. The method of claim 3, wherein said step of sensing electrical cardiac signals further comprises the step of electrically coupling said at least one electrode to the subjects heart and receiving electrical cardiac signals from the subject's heart.

5. The method of claim 4, wherein said step of positioning the catheter further comprises the step of positioning the catheter in the subject's heart in response to the received electrical cardiac signals and mapping areas of cardiac tissue region to be treated.

6. The method of claim 5, wherein said step of positioning the catheter further comprises the step of coupling the ultrasonic transducer to the cardiac tissue to be treated such that the ultrasonic energy is substantially directed to the cardiac tissue region to be treated.

7. The method of claim wherein said step of activating the ultrasonic transducer further comprises the step of applying electrical energy to said ultrasonic transducer sufficient to cause the ultrasonic transducer to resonate with frequency of about 1 to 40 MHz.

8. The method of claim 7, wherein said step of activating the ultrasonic transducer further comprises the step of resonating the ultrasonic transducer at a frequency of about 4 to 20 MHz.

9. The method of claim 7, wherein said step of applying electrical energy further comprises the step of applying at least 2 watts to the ultrasonic transducer.

10. The method of claim 9, wherein said step of applying electrical energy further comprises the step of applying about 5 to 40 watts to the ultrasonic transducer.

11. The method of claim 1, wherein said step of heating the cardiac tissue further comprises the step of creating a lesion size at least 0.5 cm$^2$.

12. The method of claim 1, wherein said step of heating further comprises the step of heating the cardiac tissue to at least about 46° C.

13. The method of claim 12, wherein said step of heating the cardiac tissue further comprises heating the cardiac tissue to a depth of up to about 10 mm.

14. A method for ablation of cardiac arrhythmias, comprising the steps of:
   A. providing a catheter comprising an ultrasonic transducer mounted on a distal region of the catheter and at least one electrode associated with the distal region of the catheter and positioned to receive electrical signals from cardiac tissue;
   B. introducing the catheter into the heart of a patient by guiding the catheter through at least one of an arterial or venous route leading to the intra-cardiac region;
   C. positioning the catheter such that the ultrasonic transducer is positioned to ultrasonically couple to a cardiac tissue region to be treated and the at least one electrode is electrically coupled to electrical signals from the cardiac tissue;

D. sensing the electrical signals from the cardiac tissue by electrically coupling the at least one electrode with the electrical signals from the cardiac tissue, electrically transmitting the received electrical signals to display means for displaying the received electrical signals and determining electrical conduction patterns of the heart;

E. applying electrical energy to the ultrasonic transducer thereby causing the ultrasonic transducer to vibrate and emit ultrasonic energy;

F. directing the ultrasonic energy at the cardiac tissue area to be treated; and G. applying sufficient ultrasonic energy to the cardiac tissue area to be treated to impart sufficient thermal energy to ablate the cardiac tissue area and alter the electrical conduction pattern in the cardiac tissue area.

15. The method of claim 14, wherein said step of positioning the catheter further comprises the step of orienting the catheter relative to the cardiac tissue to direct the ultrasonic transducer in the direction of the cardiac tissue to be treated.

16. The method of claim 15, wherein said step of orienting the catheter further comprises the step of coupling the ultrasonic transducer to the cardiac tissue to be treated such that the ultrasonic energy is directed toward the cardiac tissue region to be treated.

17. The method of claim 14, wherein said step of activating the ultrasonic transducer further comprises the step of applying electrical energy to said ultrasonic transducer sufficient to cause the ultrasonic transducer to resonate with frequency of about 1 to 40 MHz.

18. The method of claim 17, wherein said step of applying electrical energy further comprises the step of applying at least 2 watts to the ultrasonic transducer.

19. The method of claim 17, wherein said step of applying electrical energy further comprises the step of applying about 5 to 40 watts to the ultrasonic transducer.

20. The method of claim 14, wherein said step of activating the ultrasonic transducer further comprises the step of resonating the ultrasonic transducer at a frequency of about 4 to 20 MHz.

21. The method of claim 14, wherein said step of heating the cardiac tissue further comprises the step of creating a lesion size at least 0.5 cm².

22. The method of claim 14, wherein said step of heating further comprises the step of heating the cardiac tissue to at least about 46° C.

23. The method of claim 14, wherein said step of heating the cardiac tissue further comprises heating the cardiac tissue to at least about 46° C. to a depth of at least about 10 mm.

24. A catheter, comprising:

A. catheter tubing having proximal and distal ends thereof;

B. ultrasound transducer means for generating narrow band ultrasonic energy sufficient to ablate cardiac tissue, in response to an applied electrical current, said ultrasound transducer means being associated with said catheter tubing in close proximity to the distal end thereof;

C. electrode means for electrically coupling to electrical signals generated by myocardial tissue, said electrode means being coupled to said catheter in close proximity to the distal end thereof and in close proximity to said ultrasound transducer means;

D. electrical coupling means for electrically coupling said ultrasound transducer means to at least one external power source and electrically coupling said electrode means to at least one of a display or a recorder.

25. The catheter of claim 24, wherein said ultrasound transducer means further comprises ultrasound crystals adapted to generate at least one of focused ultrasound energy, collimated ultrasound energy, or diffused ultrasound energy.

26. The catheter of claim 24, wherein said ultrasound transducer means further comprises a phased array of transducer elements.

27. The catheter of claim 24, wherein said ultrasound transducer means further comprises an ultrasound transducer operable in each of a narrow band frequency for ablation and a relatively wider frequency band for imaging.

28. The catheter of claim 24, further comprising second ultrasound transducer means for providing an imaging signal.

29. The catheter of claim 24 further comprising one of a low or high impedance backing adjacent to a back surface of said ultrasound transducer.

30. The catheter of claim 29 wherein said low impedance backing is at least one of air or gas.

31. The catheter of claim 29 wherein said high impedance backing is metal.

* * * * *